(12) United States Patent
Müller et al.

(10) Patent No.: US 7,723,267 B2
(45) Date of Patent: *May 25, 2010

(54) SUBSTITUTED FLUOROALCOXYPHENYLSULFONYLUREA

(75) Inventors: Klaus-Helmut Müller, Düsseldorf (DE); Ernst-Rudolf Gesing, Erkrath (DE); Joachim Kluth, Langenfeld (DE); Mark Wilhelm Drewes, Langenfeld (DE); Peter Dahmen, Neuss (DE); Dieter Feucht, Monheim (DE); Rolf Pontzen, Leichlingen (DE); Ulrike Wachendorff-Neumann, Neuwied (DE)

(73) Assignee: Bayer CropScience AG, Monheim (DE)

(*) Notice: Subject to any disclaimer, the term of this patent is extended or adjusted under 35 U.S.C. 154(b) by 22 days.

This patent is subject to a terminal disclaimer.

(21) Appl. No.: 10/469,721

(22) PCT Filed: Feb. 27, 2002

(86) PCT No.: PCT/EP02/02064

§ 371 (c)(1), (2), (4) Date: Jan. 7, 2004

(87) PCT Pub. No.: WO02/072560

PCT Pub. Date: Sep. 19, 2002

(65) Prior Publication Data

US 2004/0097375 A1 May 20, 2004

(30) Foreign Application Priority Data

Mar. 12, 2001 (DE) ................. 101 11 649

(51) Int. Cl.
*A01N 43/54* (2006.01)
*C07D 239/02* (2006.01)

(52) U.S. Cl. .................. 504/242; 504/243; 544/242; 544/298

(58) Field of Classification Search .............. 544/1, 544/242, 298; 504/242, 243
See application file for complete search history.

(56) References Cited

U.S. PATENT DOCUMENTS

| 4,257,802 | A | 3/1981 | Levitt | 71/93 |
| 4,339,266 | A | 7/1982 | Levitt | 71/92 |
| 4,371,391 | A | 2/1983 | Levitt | 71/93 |
| 4,443,244 | A | 4/1984 | Levitt | 71/93 |
| 4,452,628 | A | 6/1984 | Adams, Jr. | 71/93 |
| 4,655,822 | A | 4/1987 | Levitt | 71/92 |
| 4,690,707 | A | 9/1987 | Föry et al. | 71/93 |
| 6,451,737 | B1 * | 9/2002 | Gesing et al. | 504/212 |
| 6,838,414 | B2 * | 1/2005 | Gesing et al. | 504/214 |

FOREIGN PATENT DOCUMENTS

| EP | 0 044 807 | 1/1982 |
| EP | 0 044 808 | 1/1982 |
| EP | 0 113 956 | 7/1984 |
| WO | WO 93/17001 | 9/1993 |
| WO | WO 97/03056 | 1/1997 |
| WO | WO 97/32861 | 9/1997 |

OTHER PUBLICATIONS

Schlaeppi et al, Development of Magnetic Particles-Based automated Chemiluminescent immunoassay for triasulfuron, J. Agricultural and Food Chemistry, 1994, 49(9), 1914-19.*

* cited by examiner

*Primary Examiner*—Alton N Pryor
(74) *Attorney, Agent, or Firm*—Richard E. L. Henderson

(57) ABSTRACT

The invention relates to substituted fluoroalkoxyphenylsulfonylureas of the general formula (I)

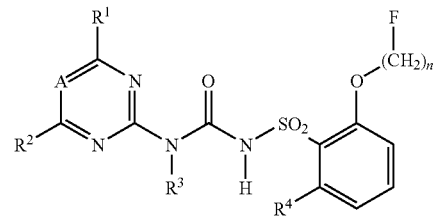

in which
n, A, $R^1$, $R^2$, $R^3$ and $R^4$ are as defined in the description,
to their use as plant treatment agents, in particular as herbicides and fungicides, and to a process and intermediates for their preparation.

8 Claims, No Drawings

SUBSTITUTED FLUOROALCOXYPHENYLSULFONYLUREA

The invention relates to novel substituted fluoroalkoxyphenylsulfonylureas, to a process for their preparation and to their use as crop treatment agents, in particular as herbicides and as fungicides.

It is already known that certain substituted sulfonylureas have herbicidal properties (cf. EP-A-1514, EP-A-23422, EP-A-44807, EP-A44808, WO-A-97/32861). However, the herbicidal activity and the compatibility of these compounds with crop plants are not entirely satisfactory. A fungicidal activity of these compounds has hitherto not been disclosed. The present invention provides the novel substituted fluoroalkoxyphenylsulfonylureas of the general formula (I)

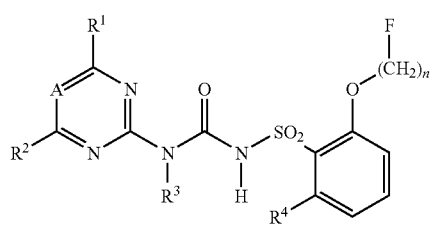

in which
n represents the numbers 2, 3 or 4,
A represents nitrogen or the grouping C—X, where
  X represents hydrogen, halogen or in each case optionally halogen-substituted alkyl or alkoxy having in each case 1 to 4 carbon atoms, or together with $R^1$ or $R^2$ represents one of the groupings —CH$_2$CH$_2$O—, —CH$_2$CH$_2$S—, —CH$_2$CH$_2$CH$_2$—,
  $R^1$ represents hydrogen, represents halogen or represents in each case optionally halogen- or $C_1$-$C_4$-alkoxy-substituted alkyl, alkoxy, alkylthio, alkylamino or dialkylamino having in each case 1 to 4 carbon atoms in the alkyl groups,
  $R^2$ represents hydrogen, represents cyano, represents halogen or represents in each case optionally halogen- or $C_1$-$C_4$-alkoxy-substituted alkyl, alkoxy, alkylthio, alkylamino or dialkylamino having in each case 1 to 4 carbon atoms in the alkyl groups, or represents cycloalkyl having 3 to 6 carbon atoms,
  $R^3$ represents hydrogen or represents optionally cyano-, halogen-, $C_1$-$C_4$-alkoxy- or $C_1$-$C_4$-alkoxycarbonyl-substituted alkyl having 1 to 4 carbon atoms, and
  $R^4$ represents halogen, represents in each case optionally cyano-, halogen- or $C_1$-$C_4$-alkoxy-substituted alkyl or alkoxy having in each case 1 to 4 carbon atoms, represents in each case optionally cyano- or halogen-substituted alkenyl, alkynyl, alkenyloxy or alkynyloxy having in each case 2 to 4 carbon atoms, or represents optionally cyano-, halogen- or $C_1$-$C_4$-alkyl-substituted cycloalkyl having 3 to 6 carbon atoms, and also salts of compounds of the formula (I).

Preferred substituents or ranges of the radicals present in the formulae shown above and below are described below:
n preferably represents the numbers 2, 3 or 4.
A preferably represents nitrogen or the grouping C—X, where
  X preferably represents hydrogen, fluorine, chlorine, bromine or in each case optionally fluorine- and/or chlorine-substituted methyl, ethyl, methoxy or ethoxy, or together with $R^1$ or $R^2$ represents one of the groupings —CH$_2$CH$_2$O—, —CH$_2$CH$_2$S—, —CH$_2$CH$_2$CH$_2$—,
  $R^1$ preferably represents hydrogen, fluorine, chlorine, bromine, or represents in each case optionally fluorine-, chlorine-, methoxy-, ethoxy- or n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.
  $R^2$ preferably represents hydrogen, cyano, fluorine, chlorine, bromine, represents in each case optionally fluorine-, chlorine-, methoxy-, ethoxy- or n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino or represents cyclopropyl, cyclobutyl, cyclopentyl or cyclohexyl.
  $R^3$ preferably represents hydrogen or represents in each case optionally cyano-, fluorine-, chlorine-, methoxy-, ethoxy-, n- or i-propoxy-, methoxycarbonyl-, ethoxycarbonyl-, n- or i-propoxycarbonyl-substituted methyl, ethyl, n- or i-propyl, n-, i-, s- or t-butyl.
  $R^4$ preferably represents fluorine, chlorine, bromine, or represents in each case optionally fluorine-, chlorine-, bromine-, methoxy-, ethoxy-, n- or i-propoxy-, n-, i-, s- or t-butoxy-substituted methyl, ethyl, n- or i-propyl, n-, i-, s- or t-butyl, methoxy, ethoxy, n- or i-propoxy, n-, i-, s- or t-butoxy, represents in each case optionally fluorine-, chlorine- and/or bromine-substituted ethenyl, propenyl, butenyl, ethynyl, propynyl, butynyl, propenyloxy, butenyloxy, propynyloxy or butynyloxy, or represents in each case optionally fluorine-, chlorine- or methyl-substituted cyclopropyl, cyclobutyl or cyclopentyl.

n particularly preferably represents the numbers 2, 3 or 4.
A particularly preferably represents nitrogen or the grouping C—X, where
  X represents hydrogen, fluorine, chlorine, methyl or methoxy, or together with $R^1$ or $R^2$ represents one of the groupings —CH$_2$CH$_2$O—, —CH$_2$CH$_2$S—, —CH$_2$CH$_2$CH$_2$—.
  $R^1$ particularly preferably represents hydrogen, fluorine, chlorine, bromine, or represents in each case optionally fluorine-, chlorine-, methoxy-, ethoxy- or n- or i-propoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino.
  $R^2$ particularly preferably represents hydrogen, cyano, fluorine, chlorine, bromine, represents in each case optionally fluorine-, chlorine-, methoxy-, ethoxy- or n- or i-propoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino or represents cyclopropyl.
  $R^3$ particularly preferably represents hydrogen or represents in each case optionally cyano-, fluorine-, chlorine-, methoxy-, ethoxy-, n- or i-propoxy-, methoxycarbonyl-, ethoxycarbonyl-, n- or i-propoxycarbonyl-substituted methyl, ethyl, n- or i-propyl.
  $R^4$ particularly preferably represents fluorine, chlorine, bromine, or represents in each case optionally fluorine-, chlorine-, methoxy-, ethoxy-, n- or i-propoxy-substituted methyl, ethyl, n- or i-propyl, methoxy, ethoxy, n- or i-propoxy, represents in each case optionally fluorine-, chlorineand/or bromine-substituted propenyl, butenyl, propynyl, butynyl, propenyloxy, butenyloxy, propynyloxy or butynyloxy, or represents optionally fluorine-, chlorine- or methyl-substituted cyclopropyl.

n very particularly preferably represents the number 2 or 3.
A very particularly preferably represents nitrogen or a CH grouping.
$R^1$ very particularly preferably represents cyano, chlorine, methyl, trifluoromethyl, ethyl, methoxy, difluoromethoxy, trifluoromethoxy, ethoxy, fluoroethoxy, difluoroethoxy, trifluoroethoxy, methylthio, ethylthio, methylamino, ethylamino, dimethylamino or cyclopropyl.
$R^2$ very particularly preferably represents chlorine, methyl, trifluoromethyl, ethyl, methoxy, difluoromethoxy, trifluoromethoxy, ethoxy, fluoroethoxy, difluoroethoxy, trifluoroethoxy, methylthio, ethylthio, methylamino, ethylamino or dimethylamino.
$R^3$ very particularly preferably represents hydrogen or methyl.
$R^4$ very particularly preferably represents fluorine, chlorine, bromine, methyl, trifluoromethyl, ethyl, n- or i-propyl, methoxy, ethoxy, n- or i-propoxy, or represents cyclopropyl.

A very particularly preferred group are those compounds of the formula (I) in which
n represents the numbers 2 or 3,
A represents nitrogen,
$R^1$ represents chlorine, methyl, trifluoromethyl, ethyl, methoxy, difluoromethoxy, trifluoromethoxy, ethoxy, fluoroethoxy, difluoroethoxy, trifluoroethoxy, methylthio, ethylthio, methylamino, ethylamino or dimethylamino,
$R^2$ represents chlorine, methyl, trifluoromethyl, ethyl, methoxy, difluoromethoxy, trifluoromethoxy, ethoxy, fluoroethoxy, difluoroethoxy, trifluoroethoxy, methylthio, ethylthio, methylamino, ethylamino or dimethylamino,
$R^3$ represents hydrogen or methyl, and
$R^4$ represents fluorine, chlorine, bromine, methyl, trifluoromethyl, ethyl, n- or i-propyl, methoxy, ethoxy, n- or i-propoxy.

A further very particularly preferred group are those compounds of the formula (I) in which
n represents the numbers 2 or 3,
A represents a CH grouping,
$R^1$ represents methyl, trifluoromethyl, ethyl, methoxy, difluoromethoxy, trifluoromethoxy, ethoxy, fluoroethoxy, difluoroethoxy, trifluoroethoxy, methylthio, ethylthio, methylamino, ethylamino or dimethylamino,
$R^2$ represents methyl, trifluoromethyl, ethyl, methoxy, difluoromethoxy, trifluoromethoxy, ethoxy, fluoroethoxy, difluoroethoxy, trifluoroethoxy, methylthio, ethylthio, methylamino, ethylamino or dimethylamino,
$R^3$ represents hydrogen or methyl, and
$R^4$ represents fluorine, chlorine, bromine, methyl, trifluoromethyl, ethyl, n- or i-propyl, methoxy, ethoxy, n- or i-propoxy.

The compounds in which n represents 3 or 4 may be mentioned as a further preferred group according to the invention.

The invention furthermore preferably provides sodium, potassium, magnesium, calcium, ammonium, $C_1$-$C_4$-alkylammonium, di-($C_1$-$C_4$-alkyl)ammonium, tri-($C_1$-$C_4$-alkyl)ammonium, tetra-($C_1$-$C_4$-alkyl)ammonium, tri-($C_1$-$C_4$-alkyl)sulfonium, $C_5$- or $C_6$-cycloalkylammonium and di-($C_1$-$C_2$-alkyl)benzylammonium salts of compounds of the formula (I), in which n, A, $R^1$, $R^2$, $R^3$ and $R^4$ have the meanings given above as being preferred.

The general or preferred radical definitions listed above apply both to the end products of the formula (I) and, correspondingly, to the starting materials or intermediates required in each case for the preparation. These radical definitions can be combined with one another as desired, i.e. including combinations between the given preferred ranges.

Preference according to the invention is given to those compounds of the formula (I) which contain a combination of the meanings listed above as being preferred ("preferable").

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

Most preference according to the invention is given to those compounds of the formula (I) which contain a combination of the meanings listed above as being most preferred.

Saturated or unsaturated hydrocarbon radicals, such as alkyl or alkenyl, are in each case straight-chain or branched as far as this is possible—including in combination with heteroatoms, such as in alkoxy.

Optionally substituted radicals may be mono- or polysubstituted, where in the case of polysubstitution the substituents may be identical or different.

The novel substituted fluoroalkoxyphenylsulfonylureas of the general formula (I) have interesting biological properties. In particular, they have strong herbicidal and fungicidal activity.

The novel substituted fluoroalkoxyphenylsulfonylureas of the general formula (I) are obtained when substituted aminoazines of the general formula (II)

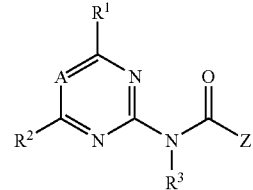

(II)

in which
A, $R^1$ and $R^2$ are as defined above,
Z represents halogen, alkoxy or aryloxy and
$R^3$ is as defined above or represents the grouping —C(O)—Z, are reacted with fluoroalkoxybenzenesulfonamides of the general formula (III)

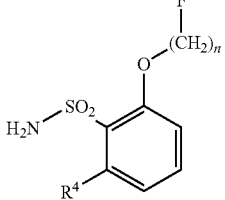

(III)

in which
n and $R^4$ are as defined above, if appropriate in the presence of one or more reaction auxiliaries and if appropriate in the presence of one or more diluents, and the resulting compounds of the general formula (I) are, if appropriate, converted into their salts by customary methods.

In principle, the novel substituted fluoroalkoxyphenylsulfonylureas of the general formula (I) can also be obtained as shown schematically below:

(b) by reacting aminoazines of the general formula (IV) with fluoroalkoxyphenylsulfonyl isocyanates of the general formula (V); n, $R^1$, $R^2$, $R^3$ and $R^4$ as above (cf. WO-A-97/32861):

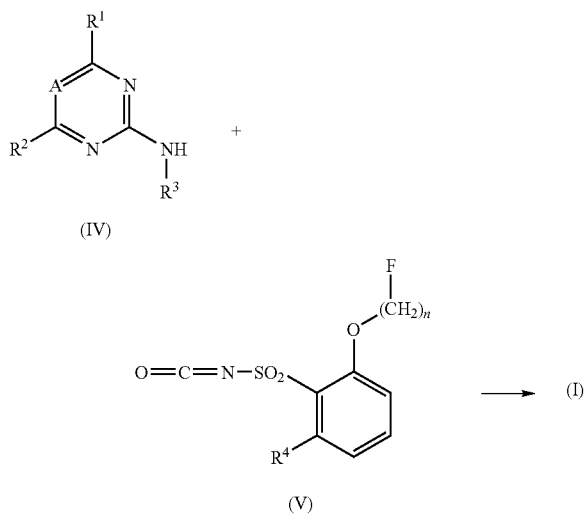

(c) by reacting aminoazines of the general formula (IV) with substituted fluoroalkoxybenzenesulfonamides of the general formula (VI); n, $R^1$, $R^2$, $R^3$ and $R^4$ as above, Z: halogen, $C_1$-$C_4$-alkoxy or phenoxy (cf. WO-A-97/32861):

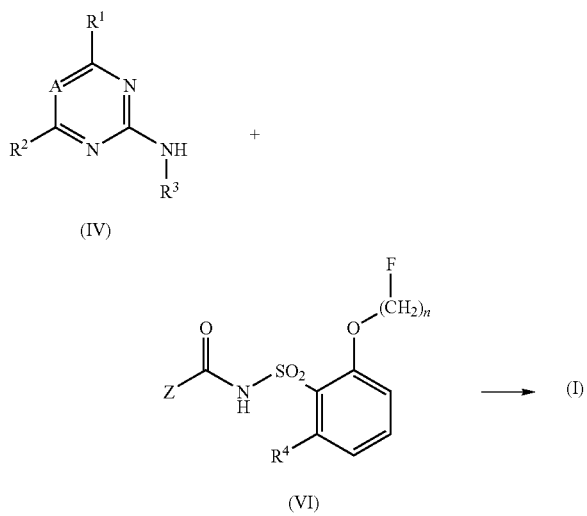

Using, for example, 2-methoxycarbonylamino-4-methoxy-6-trifluoromethyl-1,3,5-triazine and 2-(2-fluoroethoxy)-6-methylbenzenesulfonamide as starting materials, the course of the reaction in the process according to the invention can be illustrated by the formula scheme below:

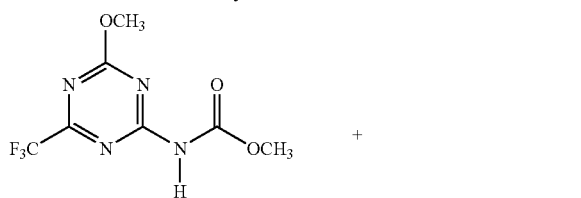

+

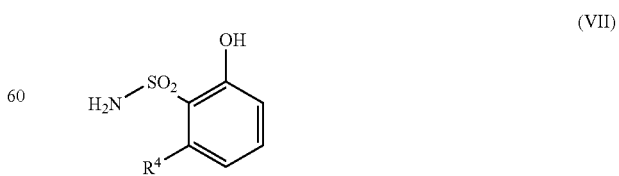

The formula (II) provides a general definition of the aminoazines to be used as starting materials in the process according to the invention for preparing compounds of the general formula (I). In the general formula (II), A, $R^1$ and $R^2$ preferably or in particular have those meanings which have already been mentioned above, in connection with the description of the compounds of the general formula (I) according to the invention, as being preferred or as being particularly preferred for A, $R^1$ and $R^2$; Z preferably represents fluorine, chlorine, bromine, $C_1$-$C_4$-alkoxy or phenoxy, in particular chlorine, methoxy, ethoxy or phenoxy.

The starting materials of the general formula (II) are known and/or can be prepared by processes known per se (cf. DE-A-19 501 174, U.S. Pat. No. 4,690,707).

The formula (III) provides a general definition of the fluoroalkoxybenzenesulfonamides further to be used as starting materials in the process according to the invention for preparing compounds of the general formula (I). In the general formula (III), n and $R^4$ preferably or in particular have those meanings which have already been mentioned above, in connection with the description of the compounds of the general formula (I) according to the invention, as being preferred or as being particularly preferred for n and $R^4$.

Some of the starting materials of the general formula (III) are known by disclosure in the form of a generic formula (cf. WO 97/03056). However, the starting materials of the formula (III) are a novel selection from among the prior-art compounds and therefore also form part of the subject matter of the present application. As a preferred group of the starting materials of the formula (III) according to the invention, mention may be made of those compounds in which n and $R^4$ do not simultaneously represent 2 and unsubstituted alkyl, respectively.

The novel fluoroalkoxybenzenesulfonamides of the general formula (III) are obtained when hydroxybenzenesulfonamides of the general formula (VII)

(VII)

[structure VII]

in which
$R^4$ is as defined above, are reacted with with ω-fluoro-α-haloalkanes of the general formula (VIII)

in which
n is as defined above and
X represents halogen, preferably chlorine, bromine or iodine, in particular bromine, or represents methylsulfonyloxy, phenylsulfonyloxy or tolylsulfonyloxy, if appropriate in the presence of a diluent, such as, for example, acetone, butanone, acetonitrile, propionitrile, N,N-dimethylformamide or N,N-dimethylacetamide, and if appropriate in the presence of an acid acceptor, such as, for example, potassium carbonate, at temperatures between 0° C. and 150° C. (cf. the Preparation Examples). The hydroxybenzenesulfonamides of the general formula (VII) are known and/or can be prepared by processes known per se (cf. EP-A-44807, WO-A-97/03056).

The ω-fluoro-α-haloalkanes of the general formula (VIII) further required as precursors are known organic chemicals for synthesis.

The process according to the invention for preparing the novel substituted fluoroalkoxyphenylsulfonylureas of the general formula (III) is preferably carried out in the presence of one or more reaction auxiliaries. Reaction auxiliaries suitable for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]octane (DABCO), 1,5-diazabicyclo[4.3.0]non-5-ene (DBN) or 1,8 diazabicyclo[5.4.0]-undec-7-ene (DBU).

Further suitable reaction auxiliaries for the process according to the invention include phase-transfer catalysts. Examples of such catalysts which may be mentioned are:

tetrabutylammonium bromide, tetrabutylammonium chloride, tetraoctylammonium chloride, tetrabutylammonium hydrogen sulfate, methyltrioctylammonium chloride, hexadecyltrimethylammonium chloride, hexadecyltrimethylammonium bromide, benzyltrimethylammonium chloride, benzyltriethylammonium chloride, benzyltrimethylammonium hydroxide, benzyltriethylammonium hydroxide, benzyltributylammonium chloride, benzyltributylammonium bromide, tetrabutylphosphonium bromide, tetrabutylphosphonium chloride, tributylhexadecylphosphonium bromide, butyltriphenylphosphonium chloride, ethyltrioctylphosphonium bromide, tetraphenylphosphonium bromide.

The process according to the invention for preparing the compounds of the general formula (I) is preferably carried out using one or more diluents. Suitable diluents for carrying out the process according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diusopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulfoxides, such as dimethyl sulfoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the process according to the invention, the reaction temperatures can be varied within a relatively wide range. In general, the process is carried out at temperatures between 0° C. and 150° C., preferably between 10° C. and 120° C.

In general, the process according to the invention is carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

If appropriate, salts may be prepared from the compounds of the general formula (I) according to the invention. Such salts are obtained in a simple manner by customary methods for forming salts, for example by dissolving or dispersing a compound of the formula (I in a suitable solvent, such as, for example, methylene chloride, acetone, tert-butyl methyl ether or toluene, and adding a suitable base, such as, for example, sodium hydroxide. The salts can then—if appropriate after prolonged stirring—be isolated by concentration or by filtration with suction (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis,*

*Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without trees. Similarly, the active compounds according to the invention can be employed for controlling weeds in perennial crops, for example forests, decorative tree plantations, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. To a certain extent, they also induce resistance. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants may be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are: for example, ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example, lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, amitrole, anilofos, asulam, atrazine, azafenidin, azimsulfuiron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromacil, bromobutide, bromofenoxim, bromoxynil, butachlor, butafenacil (-allyl), butenachlor, butralin, butroxydim, butylate, cafenstrole, carbetamide, carfentrazone (-ethyl), chlomethoxyfen, chloramben, chloridazon, chlorimuron (-ethyl), chlornitrofen, chlorsulfuron, chlorthiamid, chlortoluron, cinidon (-ethyl), cinmethylin, cinosulfuron, clefoxydim, clethodim, clodinafop (-propargyl), cloimazone, clomeprop, clopyralid, cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlobenil, dichlorprop (-P), diclofop (-methyl), diclosulam, diethatyl (-ethyl), difenopenten (-ethyl), difenzoquat, diflufenican, diflufenzopyr, dikegulac (-sodium), dimefuron, dimepiperate, dimethachlor, dimethametryn, dimethenamid (-P), dimexyflam, dinitramine, diphenamid, diquat (-dibromide), dithiopyr, diuron, dymron, epropodan, EPTC, esprocarb, ethalfluralin, ethametsulfuron (-methyl), ethiozin, ethofumesate, ethoxyfen, ethoxysulfuron, etobenzanid, fenoxaprop (-P-ethyl), fentrazamide, flamprop (-M-isopropyl, -M-methyl), flazasulfuron, florasulam, fluazifop (-P-butyl), fluazolate, flucarbazone (-sodium), fluchloralin, flufenacet, flumetsulam, flumiclorac (-pentyl), flumioxazin, flumipropyn, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fomesafen, foramsulfuron, glufosinate (-ammonium), glyphosate (-ammonium, -isopropylammonium), halosafen, halosulfuron (-methyl), haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxadifen (-ethyl), isoxaflutole, isoxapyrifop, ketospiradox, lactofen, lenacil, linuron, MCPA, mecoprop (-P), mefenacet, mesotrione, metamitron, metazachlor, methabenzthiazuron, methyldymron, metobenzuron, metobroimuron, (S-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, pethoxamid, phenmedipham, picolinafen, piperophos, pretilachlor, primisulfuron (-methyl), profluazol, profoxydim, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridafol, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiazopyr, thidiazimin, thifensulfuron (-methyl), thiobencarb, tiocarbazil, tralkoxydim, triallate, triasulfuron, tribenuron (-methyl), triclopyr, tridiphane, trifloxysulfuron, trifluralin, triflusulfuron (-methyl), tritosulfuron.

Furthermore suitable for the mixtures are known safeners, for example

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is shown in the examples below.

PREPARATION EXAMPLES

Example 1

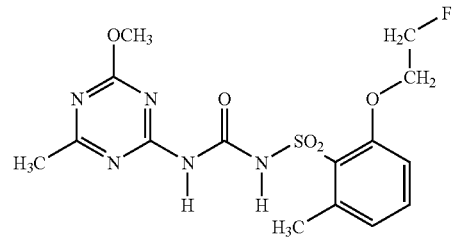

At room temperature (about 20° C.), a solution of 23.4 g (154 mmol) of 1,8 diazabicyclo[5.4.0]undec-7-ene (DBU) in 50 ml of acetonitrile is added dropwise with stirring to a mixture of 32.7 g (140 mmol) of 2-(2-fluoroethoxy)-6-methylbenzenesulfonamide, 53.2 g (140 mmol) of 2-(N,N-bisphenoxycarbonylamino)-4-methoxy-6-methyl-1,3,5-triazine and 300 ml of acetonitrile. The reaction mixture is stirred at room temperature for one hour and then concentrated under reduced pressure. The residue is taken up in 300 ml of methylene chloride and shaken with 1N hydrochloric acid, then with water and finally with saturated aqueous sodium chloride solution. The organic phase is then dried using sodium sulfate and filtered. The filtrate is concentrated and the residue is digested with 100 ml of diethyl ether. The resulting crystalline product is isolated by filtration with suction.

This gives 36.9 g (60% of theory) of N-[2-(2-fluoroethoxy)-6-methylphenylsulfonyl]-N'-(4-methoxy-6-1,3,5-triazin-2-yl)urea of melting point 161° C.

Example 2

At room temperature, 3.3 g (82 mmol) of sodium hydroxide (Micropills) are added with stirring to a mixture of 36.0 g (82 mmol) of N-[2-(2-fluoroethoxy)-6-methylphenylsulfonyl]-N'-(4-methoxy-6-methyl-1,3,5-triazin-2-yl)urea and 250 ml of methylene chloride. The mixture is stirred at room temperature for about 20 hours; the resulting crystalline product is then isolated by filtration with suction.

This gives 36.9 g (100% of theory) of N-[2-(2-fluoroethoxy)-6-methylphenylsulfonyl]-N'-(4-methoxy-6-methyl-1, 3,5-triazin-2-yl)urea sodium salt of melting point 185° C.

Analogously to examples 1 and 2, and in accordance with the general description of the preparation process according to the invention, it is also possible to prepare, for example, the compounds of the general formula (I) listed in table 1 below.

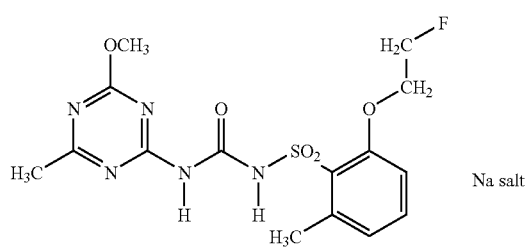

Na salt

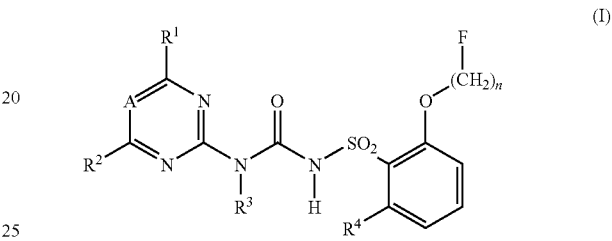

(I)

TABLE 1

Examples of compounds of the formula (I)

| Ex. No. | n | A | R$^1$ | R$^2$ | R$^3$ | R$^4$ | Physical data |
|---|---|---|---|---|---|---|---|
| 3 | 2 | N | CH$_3$ | OCH$_3$ | H | CF$_3$ | m.p.: 124° C. |
| 4 | 2 | CH | OCH$_3$ | OCH$_3$ | H | CF$_3$ | m.p.: 183° C. |
| 5 | 2 | N | CH$_3$ | OCH$_3$ | H | CF$_3$ | m.p.: 187° C. (Na salt) |
| 6 | 3 | CH | CH$_3$ | CH$_3$ | H | C$_2$H$_5$ | m.p.: 213° C. |
| 7 | 3 | N | CH$_3$ | OCH$_3$ | H | C$_3$H$_7$-n | m.p.: 109° C. |
| 8 | 3 | N | OCH$_3$ | OCH$_3$ | H | C$_3$H$_7$-n | m.p.: 139° C. |
| 9 | 3 | N | OCH$_2$CF$_3$ | N(CH$_3$)$_2$ | H | CH$_3$ | m.p.: 180° C. |
| 10 | 3 | N | OCH$_2$CF$_3$ | N(CH$_3$)$_2$ | H | C$_2$H$_5$ | m.p.: 113° C. |
| 11 | 3 | N | OCH$_2$CF$_3$ | N(CH$_3$)$_2$ | H | C$_3$H$_7$-n | m.p.: 172° C. |
| 12 | 3 | CH | OCH$_3$ | OCH$_3$ | H | CH$_3$ | m.p.: 142° C. |
| 13 | 3 | N | CH$_3$ | OCH$_3$ | H | CH$_3$ | m.p.: 170° C. |
| 14 | 3 | CH | Cl | OCH$_3$ | H | CH$_3$ | m.p.: 163° C. |
| 15 | 3 | N | OCH$_3$ | OCH$_3$ | H | CH$_3$ | m.p.: 155° C. |
| 16 | 3 | CH | OCH$_3$ | OCH$_3$ | H | C$_2$H$_5$ | m.p.: 154° C. |
| 17 | 3 | N | CH$_3$ | OCH$_3$ | H | C$_2$H$_5$ | m.p.: 121° C. |
| 18 | 3 | CH | Cl | OCH$_3$ | H | C$_2$H$_5$ | m.p.: 139° C. |
| 19 | 3 | N | OCH$_3$ | OCH$_3$ | H | C$_2$H$_5$ | m.p.: 130° C. |
| 20 | 2 | CH | Cl | OCH$_3$ | H | CF$_3$ | m.p.: 123° C. |
| 21 | 2 | N | OCH$_3$ | OCH$_3$ | H | CF$_3$ | m.p.: 169° C. |
| 22 | 2 | N | OCH$_2$CF$_3$ | N(CH$_3$)$_2$ | H | CF$_3$ | m.p.: 162° C. |
| 23 | 2 | N | OCH$_3$ | OCH$_3$ | CH$_3$ | CF$_3$ | m.p.: 176° C. |
| 24 | 2 | CH | OCH$_3$ | OCH$_3$ | H | CH$_3$ | m.p.: 169° C. |
| 25 | 3 | CH | OCH$_3$ | OCH$_3$ | H | C$_3$H$_7$-n | m.p.: 114° C. |
| 26 | 2 | CH | OCH$_3$ | OCH$_3$ | H | C$_3$H$_7$-n | m.p.: 166° C. |
| 27 | 2 | N | CH$_3$ | OCH$_3$ | CH$_3$ | CF$_3$ | m.p.: 177° C. |
| 28 | 3 | N | CH$_3$ | OCH$_3$ | CH$_3$ | C$_2$H$_5$ | m.p.: 124° C. |
| 29 | 3 | N | CH$_3$ | OCH$_3$ | CH$_3$ | CH$_3$ | m.p.: 146° C. |
| 30 | 3 | N | OCH$_3$ | OCH$_3$ | CH$_3$ | C$_2$H$_5$ | m.p.: 168° C. |
| 31 | 3 | N | OCH$_3$ | OCH$_3$ | CH$_3$ | C$_3$H$_7$-n | m.p.: 150° C. |
| 32 | 3 | N | OCH$_3$ | OCH$_3$ | CH$_3$ | CH$_3$ | m.p.: 165° C. |
| 33 | 2 | CH | CH$_3$ | CH$_3$ | H | CH$_3$ | |
| 34 | 2 | N | CH$_3$ | CH$_3$ | H | CH$_3$ | |
| 35 | 2 | CH | CH$_3$ | OCH$_3$ | H | CH$_3$ | |
| 36 | 2 | N | OCH$_3$ | OCH$_3$ | H | CH$_3$ | |
| 37 | 2 | N | OCH$_2$CF$_3$ | N(CH$_3$)$_2$ | H | CH$_3$ | |
| 38 | 2 | CH | Cl | OCH$_3$ | H | CH$_3$ | |
| 39 | 2 | CH | CH$_3$ | CH$_3$ | H | C$_2$H$_5$ | |
| 40 | 2 | N | CH$_3$ | CH$_3$ | H | C$_2$H$_5$ | |
| 41 | 2 | CH | CH$_3$ | OCH$_3$ | H | C$_2$H$_5$ | |

TABLE 1-continued

Examples of compounds of the formula (I)

| Ex. No. | n | A | R¹ | R² | R³ | R⁴ | Physical data |
|---|---|---|---|---|---|---|---|
| 42 | 2 | N | CH₃ | OCH₃ | H | C₂H₅ | |
| 43 | 2 | CH | OCH₃ | OCH₃ | H | C₂H₅ | |
| 44 | 2 | N | OCH₃ | OCH₃ | H | C₂H₅ | |
| 45 | 2 | N | OCH₂CF₃ | N(CH₃)₂ | H | C₂H₅ | |
| 46 | 2 | CH | Cl | OCH₃ | H | C₂H₅ | |
| 47 | 2 | CH | CH₃ | CH₃ | R | C₃H₇-n | |
| 48 | 2 | N | CH₃ | CH₃ | R | C₃H₇-n | |
| 49 | 2 | CH | CH₃ | OCH₃ | R | C₃H₇-n | |
| 50 | 2 | N | CH₃ | OCH₃ | R | C₃H₇-n | |
| 51 | 2 | N | OCH₃ | OCH₃ | R | C₃H₇-n | |
| 52 | 2 | N | OCH₂CF₃ | N(CH₃)₂ | H | C₃H₇-n | |
| 53 | 2 | CH | Cl | OCH₃ | R | C₃H₇-n | |
| 54 | 2 | CH | CH₃ | CH₃ | H | C₃H₇-i | |
| 55 | 2 | N | CH₃ | CH₃ | R | C₃H₇-i | |
| 56 | 2 | CH | CH₃ | OCH₃ | H | C₃H₇-i | |
| 57 | 2 | N | CH₃ | OCH₃ | H | C₃H₇-i | |
| 58 | 2 | CH | OCH₃ | OCH₃ | H | C₃H₇-i | |
| 59 | 2 | N | OCH₃ | OCH₃ | H | C₃H₇-i | |
| 60 | 2 | N | OCH₂CF₃ | N(CH₃)₂ | H | C₃H₇-i | |
| 61 | 2 | CH | Cl | OCH₃ | H | C₃H₇-i | |
| 62 | 2 | CH | CH₃ | CH₃ | H | CF₃ | m.p.: 168° C. |
| 63 | 2 | N | CH₃ | CH₃ | H | CF₃ | |
| 64 | 2 | CH | CH₃ | OCH₃ | H | CF₃ | m.p.: 176° C. |
| 65 | 2 | CH | CH₃ | CH₃ | H | Br | |
| 66 | 2 | N | CH₃ | CH₃ | H | Br | |
| 67 | 2 | CH | CH₃ | OCH₃ | H | Br | |
| 68 | 2 | N | CH₃ | OCH₃ | H | Br | |
| 69 | 2 | CH | OCH₃ | OCH₃ | H | Br | |
| 70 | 2 | N | OCH₃ | OCH₃ | H | Br | |
| 71 | 2 | N | OCH₂CF₃ | N(CH₃)₂ | H | Br | |
| 72 | 2 | CH | Cl | OCH₃ | H | Br | |
| 73 | 2 | CH | CH₃ | CH₃ | H | OCH₃ | |
| 74 | 2 | N | CH₃ | CH₃ | H | OCH₃ | |
| 75 | 2 | CH | CH₃ | OCH₃ | H | OCH₃ | |
| 76 | 2 | N | CH₃ | OCH₃ | H | OCH₃ | |
| 77 | 2 | CH | OCH₃ | OCH₃ | H | OCH₃ | |
| 78 | 2 | N | OCH₃ | OCH₃ | H | OCH₃ | |
| 79 | 2 | N | OCH₂CF₃ | N(CH₃)₂ | H | OCH₃ | |
| 80 | 2 | CH | Cl | OCH₃ | H | OCH₃ | |
| 81 | 2 | CH | CH₃ | CH₃ | H | OC₂H₅ | |
| 82 | 2 | N | CH₃ | CH₃ | H | OC₂H₅ | |
| 83 | 2 | CH | CH₃ | OCH₃ | H | OC₂H₅ | |
| 84 | 2 | N | CH₃ | OCH₃ | H | OC₂H₅ | |
| 85 | 2 | CH | OCH₃ | OCH₃ | H | OC₂H₅ | |
| 86 | 2 | N | OCH₃ | OCH₃ | H | OC₂H₅ | |
| 87 | 2 | N | OCH₂CF₃ | N(CH₃)₂ | H | OC₂H₅ | |
| 88 | 2 | CH | Cl | OCH₃ | H | OC₂H₅ | |
| 89 | 3 | CH | CH₃ | CH₃ | H | CH₃ | |
| 90 | 3 | N | CH₃ | CH₃ | H | CH₃ | |
| 91 | 3 | CH | CH₃ | OCH₃ | H | CH₃ | |
| 92 | 3 | N | CH₃ | CH₃ | H | C₂H₅ | |
| 93 | 3 | CH | CH₃ | OCH₃ | H | C₂H₅ | |
| 94 | 3 | CH | CH₃ | CH₃ | H | C₃H₇-n | |
| 95 | 3 | N | CH₃ | CH₃ | H | C₃H₇-n | |
| 96 | 3 | CH | CH₃ | OCH₃ | H | C₃H₇-n | |
| 97 | 3 | CH | Cl | OCH₃ | H | C₃H₇-n | |
| 98 | 3 | CH | CH₃ | CH₃ | H | C₃H₇-i | |
| 99 | 3 | N | CH₃ | CH₃ | H | C₃H₇-i | |
| 100 | 3 | CH | CH₃ | OCH₃ | H | C₃H₇-i | |
| 101 | 3 | N | CH₃ | OCH₃ | H | C₃H₇-i | |
| 102 | 3 | N | CH₃ | OCH₃ | CH₃ | C₃H₇-i | |
| 103 | 3 | CH | OCH₃ | OCH₃ | H | C₃H₇-i | |
| 104 | 3 | N | OCH₃ | OCH₃ | H | C₃H₇-i | |
| 105 | 3 | N | OCH₂CF₃ | N(CH₃)₂ | H | C₃H₇-i | |
| 106 | 3 | CH | Cl | OCH₃ | H | C₃H₇-i | |
| 107 | 3 | CH | CH₃ | CH₃ | H | CF₃ | |
| 108 | 3 | N | CH₃ | CH₃ | H | CF₃ | |
| 109 | 3 | CH | CH₃ | OCH₃ | H | CF₃ | |
| 110 | 3 | N | CH₃ | OCH₃ | H | CF₃ | m.p.: 68° C. |
| 111 | 3 | N | CH₃ | OCH₃ | CH₃ | CF₃ | m.p.: 113° C. |
| 112 | 3 | CH | OCH₃ | OCH₃ | H | CF₃ | m.p.: 189° C. |
| 113 | 3 | N | OCH₃ | OCH₃ | H | CF₃ | m.p.: 138° C. |
| 114 | 3 | N | OCH₂CF₃ | N(CH₃)₂ | H | CF₃ | |
| 115 | 3 | CH | Cl | OCH₃ | H | CF₃ | |

TABLE 1-continued

Examples of compounds of the formula (I)

| Ex. No. | n | A | R¹ | R² | R³ | R⁴ | Physical data |
|---|---|---|---|---|---|---|---|
| 116 | 3 | CH | $CH_3$ | $CH_3$ | H | Br | |
| 117 | 3 | N | $CH_3$ | $CH_3$ | H | Br | |
| 118 | 3 | N | $CH_3$ | $OCH_3$ | H | Br | |
| 119 | 3 | CH | $CH_3$ | $OCH_3$ | H | Br | |
| 120 | 3 | N | $CH_3$ | $OCH_3$ | $CH_3$ | Br | |
| 121 | 3 | CH | $OCH_3$ | $OCH_3$ | H | Br | |
| 122 | 3 | N | $OCH_3$ | $OCH_3$ | H | Br | |
| 123 | 3 | N | $OCH_2CF_3$ | $N(CH_3)_2$ | H | Br | |
| 124 | 3 | CH | Cl | $OCH_3$ | H | Br | |
| 125 | 3 | CH | $CH_3$ | $CH_3$ | H | $OCH_3$ | |
| 126 | 3 | N | $CH_3$ | $CH_3$ | H | $OCH_3$ | |
| 127 | 3 | CH | $CH_3$ | $OCH_3$ | H | $OCH_3$ | |
| 128 | 3 | N | $CH_3$ | $OCH_3$ | H | $OCH_3$ | |
| 129 | 3 | N | $CH_3$ | $OCH_3$ | $CH_3$ | $OCH_3$ | |
| 130 | 3 | CH | $OCH_3$ | $OCH_3$ | H | $OCH_3$ | |
| 131 | 3 | N | $OCH_3$ | $OCH_3$ | H | $OCH_3$ | |
| 132 | 3 | N | $OCH_2CF_3$ | $N(CH_3)_2$ | H | $OCH_3$ | |
| 133 | 3 | CH | Cl | $OCH_3$ | H | $OC_2H_5$ | |
| 134 | 3 | CH | $CH_3$ | $CH_3$ | H | $OC_2H_5$ | |
| 135 | 3 | N | $CH_3$ | $CH_3$ | H | $OC_2H_5$ | |
| 136 | 3 | N | $CH_3$ | $OCH_3$ | H | $OC_2H_5$ | |
| 137 | 3 | N | $CH_3$ | $OCH_3$ | $CH_3$ | $OC_2H_5$ | |
| 138 | 3 | CH | $CH_3$ | $OCH_3$ | H | $OC_2H_5$ | |
| 139 | 3 | CH | $OCH_3$ | $OCH_3$ | H | $OC_2H_5$ | |
| 140 | 3 | N | $OCH_3$ | $OCH_3$ | H | $OC_2H_5$ | |
| 141 | 3 | N | $OCH_2CF_3$ | $N(CH_3)_2$ | H | $OC_2H_5$ | |
| 142 | 3 | CH | Cl | $OCH_3$ | H | $OC_2H_5$ | |
| 143 | 4 | N | $CH_3$ | $OCH_3$ | H | $CH_3$ | |
| 144 | 4 | CH | $CH_3$ | $OCH_3$ | H | $CH_3$ | |
| 145 | 4 | N | $CH_3$ | $OCH_3$ | $CH_3$ | $CH_3$ | |
| 146 | 4 | CH | $OCH_3$ | $OCH_3$ | H | $CH_3$ | |
| 147 | 4 | N | $OCH_3$ | $OCH_3$ | H | $CH_3$ | |
| 148 | 4 | CH | Cl | $OCH_3$ | H | $CH_3$ | |
| 149 | 4 | CH | $CH_3$ | $OCH_3$ | H | $C_2H_5$ | |
| 150 | 4 | N | $CH_3$ | $OCH_3$ | H | $C_2H_5$ | |
| 151 | 4 | N | $CH_3$ | $OCH_3$ | $CH_3$ | $C_2H_5$ | |
| 152 | 4 | CH | $CH_3$ | $OCH_3$ | H | $C_2H_5$ | |
| 153 | 4 | CH | Cl | $OCH_3$ | H | $C_2H_5$ | |
| 154 | 4 | CH | $CH_3$ | $OCH_3$ | H | $C_3H_7$-n | |
| 155 | 4 | N | $CH_3$ | $OCH_3$ | H | $C_3H_7$-n | |
| 156 | 4 | N | $CH_3$ | $OCH_3$ | $CH_3$ | $C_3H_7$-n | |
| 157 | 4 | CH | $OCH_3$ | $OCH_3$ | H | $C_3H_7$-n | |
| 158 | 4 | N | $OCH_3$ | $OCH_3$ | H | $C_3H_7$-n | |
| 159 | 4 | CH | $OCH_3$ | $OCH_3$ | H | $C_2H_5$ | |
| 160 | 4 | N | $OCH_3$ | $OCH_3$ | H | $C_2H_5$ | |
| 161 | 4 | CH | $CH_3$ | $CH_3$ | H | $CH_3$ | |
| 162 | 4 | CH | $CH_3$ | $CH_3$ | H | $C_2H_5$ | |
| 163 | 4 | CH | $CH_3$ | $CH_3$ | H | $C_3H_7$-n | |
| 164 | 4 | CH | $CH_3$ | $CH_3$ | H. | $C_3H_7$-i | |
| 165 | 4 | N | $CH_3$ | $OCH_3$ | H. | $C_3H_7$-i | |
| 166 | 4 | N | $CH_3$ | $OCH_3$ | $CH_3$ | $C_3H_7$-i | |
| 167 | 4 | GH | $CH_3$ | $OCH_3$ | H | $C_3H_7$-i | |
| 168 | 4 | CH | $OCH_3$ | $OCH_3$ | H | $C_3H_7$-i | |
| 169 | 4 | N | $OCH_3$ | $OCH_3$ | H | $C_3H_7$-i | |
| 170 | 4 | CH | Cl | $OCH_3$ | H | $C_3H_7$-i | |
| 171 | 4 | CH | $CH_3$ | $CH_3$ | H | $CF_3$ | |
| 172 | 4 | N | $CH_3$ | $CH_3$ | H | $CF_3$ | |
| 173 | 4 | CH | $CH_3$ | $OCH_3$ | H | $CF_3$ | |
| 174 | 4 | N | $CH_3$ | $OCH_3$ | H | $CF_3$ | |
| 175 | 4 | N | $CH_3$ | $OCH_3$ | $CH_3$ | $CF_3$ | |
| 176 | 4 | CH | $OCH_3$ | $OCH_3$ | H | $CF_3$ | |
| 177 | 4 | N | $OCH_3$ | $OCH_3$ | H | $CF_3$ | |
| 178 | 4 | CH | Cl | $OCH_3$ | H | $CF_3$ | |
| 179 | 2 | CH | $OCHF_2$ | $OCHF_2$ | H | $CH_3$ | |
| 180 | 2 | CH | $OCHF_2$ | $OCHF_2$ | H | $C_2H_5$ | |
| 181 | 2 | CH | $OCHF_2$ | $OCHF_2$ | H | $C_3H_7$-n | |
| 182 | 2 | CH | $OCHF_2$ | $OCHF_2$ | H | $C_3H_7$-i | |
| 183 | 2 | CH | $OCHF_2$ | $OCHF_2$ | H | $CF_3$ | |
| 184 | 2 | CH | $OCHF_2$ | $OCHF_2$ | H | Br | |
| 185 | 2 | CH | $OCHF_2$ | $OCHF_2$ | H | $OCH_3$ | |
| 186 | 2 | CH | $OCHF_2$ | $OCHF_2$ | H | $OC_2H_5$ | |
| 187 | 3 | CH | $OCHF_2$ | $OCHF_2$ | H | $CH_3$ | |
| 188 | 3 | CH | $OCHF_2$ | $OCHF_2$ | H | $C_2H_5$ | |
| 189 | 3 | CH | $OCHF_2$ | $OCHF_2$ | H | $C_3H_7$-n | |

TABLE 1-continued

Examples of compounds of the formula (I)

| Ex. No. | n | A | $R^1$ | $R^2$ | $R^3$ | $R^4$ | Physical data |
|---|---|---|---|---|---|---|---|
| 190 | 3 | CH | $OCHF_2$ | $OCHF_2$ | H | $C_3H_7$-i | |
| 191 | 3 | CH | $OCHF_2$ | $OCHF_2$ | H | $CF_3$ | |
| 192 | 3 | CH | $OCHF_2$ | $OCHF_2$ | H | Br | |
| 193 | 3 | CH | $OCHF_2$ | $OCHF_2$ | H | $OCH_3$ | |
| 194 | 3 | CH | $OCHF_2$ | $OCHF_2$ | H | $OC_2H_5$ | |
| 195 | 4 | CH | $OCHF_2$ | $OCHF_2$ | H | $CH_3$ | |
| 196 | 4 | CH | $OCHF_2$ | $OCHF_2$ | H | $C_2H_5$ | |
| 197 | 4 | CH | $OCHF_2$ | $OCHF_2$ | H | $C_3H_7$-n | |
| 198 | 4 | CH | $OCHF_2$ | $OCHF_2$ | H | $C_3H_7$-i | |
| 199 | 4 | CH | $OCHF_2$ | $OCHF_2$ | H | $CF_3$ | |
| 200 | 4 | CH | $OCHF_2$ | $OCHF_2$ | H | Br | |
| 201 | 4 | CH | $OCHF_2$ | $OCHF_2$ | H | $OCH_3$ | |
| 202 | 4 | CH | $OCHF_2$ | $OCHF_2$ | H | $OC_2H_5$ | |
| 203 | 2 | N | $C_2H_5$ | $OCH_3$ | H | $CF_3$ | m.p.: 168° C. |
| 204 | 2 | N | $CH_3$ | $OC_2H_5$ | H | $CF_3$ | m.p.: 137° C. |
| 205 | 2 | N | $CH_3$ | $N(CH_3)_2$ | H | $CF_3$ | m.p.: 93° C. |
| 206 | 2 | N | $SCH_3$ | $N(CH_3)_2$ | H | $CF_3$ | m.p.: 249° C. |
| 207 | 2 | N | $NHCH_3$ | CN | H | $CF_3$ | m.p.: 220° C. |
| 208 | 2 | N | $CH_3$ | $SCH_3$ | H | $CF_3$ | m.p.: 75° C. |
| 209 | 2 | N | $OCH_3$ | cyclopropyl | H | $CF_3$ | m.p.: 189° C. |
| 210 | 2 | N | $SCH_3$ | cyclopropyl | H | $CF_3$ | m.p.: 184° C. |
| 211 | 2 | N | $SCH_3$ | $C_3H_7$-i | H | $CF_3$ | m.p.: 86° C. |
| 212 | 2 | N | $SCH_3$ | $C_4H_9$-t | H | $CF_3$ | m.p.: 95° C. |
| 213 | 2 | CH | Cl | Cl | H | $CF_3$ | m.p.: 84° C. |
| 214 | 2 | C—Cl | H | $CH_3$ | H | $CF_3$ | m.p.: 178° C. |
| 215 | 2 | C—Br | $CH_3$ | $SCH_3$ | H | $CF_3$ | m.p.: 219° C. |
| 216 | 2 | C—Br | $CH_3$ | $OCH_3$ | H | $CF_3$ | m.p.: 215° C. |
| 217 | 2 | C—Cl | $CH_3$ | $CH_3$ | H | $CF_3$ | m.p.: 191° C. |
| 218 | 2 | C—Cl | $CH_3$ | $OCH_3$ | H | $CF_3$ | m.p.: 229° C. |
| 219 | 2 | CH | $OC_2H_5$ | $OC_2H_5$ | H | $CF_3$ | m.p.: 153° C. |
| 220 | 2 | C—X | $OCH_3$ | $R^2 + X$: —$(CH_2)_3$— | H | $CF_3$ | m.p.: 209° C. |
| 221 | 2 | C—X | Cl | $R^2 + X$: —$(CH_2)_3$— | H | $CF_3$ | m.p.: 212° C. |
| 222 | 2 | C—$CH_3$ | $CH_3$ | $OCH_3$ | H | $CF_3$ | m.p.: 215° C. |
| 223 | 2 | C—$CH_3$ | H | $C_2H_5$ | H | $CF_3$ | m.p.: 220° C. |
| 224 | 2 | C—$CH_3$ | $CH_3$ | $CH_3$ | H | $CF_3$ | m.p.: 212° C. |
| 225 | 2 | N | $CH_3$ | $OCH_3$ | H | $CF_3$ | m.p.: 208° C. Na salt) |
| 226 | 3 | N | $OCH_3$ | $OCH_3$ | $CH_3$ | $CF_3$ | m.p.: 174° C. |

Starting Materials of the Formula (III)

Example (III-1)

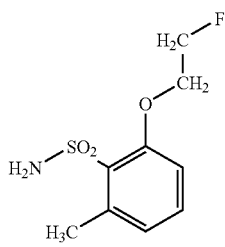

A mixture of 11.2 g (60 mmol) of 2-hydroxy-6-methylbenzenesulfonamide, 10 g (78 mmol) of 1-bromo-2-fluoroethane, 16.6 g (120 mmol) of potassium carbonate and 350 ml of acetone is heated under reflux for 48 hours and then filtered while hot. The filtrate is concentrated under reduced pressure and the residue is taken up in methylene chloride, washed with water, dried with sodium sulfate and filtered. The filtrate is concentrated, the residue is digested with diethyl ether and the resulting crystalline product is isolated by filtration with suction.

This gives 7.9 g (56% of theory) of 2-(2-fluoroethoxy)-6-methylbenzenesulfonamide of melting point 103° C.

Analogously to example (III-1), it is also possible to prepare, for example, the compounds of the general formula (III) listed in table 2 below.

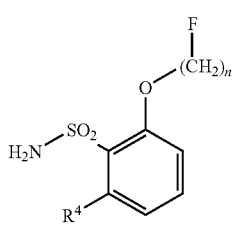

(III)

TABLE 2

Examples of compounds of the formula (III)

| Ex. No. | n | R⁴ | Melting point (° C.) |
|---|---|---|---|
| III-2 | 2 | $C_2H_5$ | 108 |
| III-3 | 2 | $CF_3$ | |
| III-4 | 2 | $C_3H_7$-i | 114 |
| III-5 | 2 | $OC_2H_5$ | 140 |
| III-6 | 2 | $C_3H_7$-n | 117 |
| III-7 | 3 | $C_3H_7$-n | 108 |
| III-8 | 2 | Br | |
| III-9 | 3 | $C_2H_5$ | 92 |
| III-10 | 3 | $CH_3$ | 118 |
| III-11 | 3 | $C_3H_7$-i | |
| III-12 | 3 | $CF_3$ | |
| III-13 | 3 | Br | |
| III-14 | 3 | $OCH_3$ | |
| III-15 | 2 | $OCH_3$ | |
| III-16 | 2 | $OC_3H_7$-n | |
| III-17 | 2 | $OC_3H_7$-i | |
| III-18 | 3 | $OC_2H_5$ | |
| III-19 | 3 | $OC_3H_7$-n | |
| III-20 | 3 | $OC_3H_7$-i | |
| III-21 | 2 | $CH_2CF_3$ | |
| III-22 | 3 | $CH_2CF_3$ | |
| III-23 | 2 | Cl | |
| III-24 | 3 | Cl | |
| III-25 | 2 | Br | |
| III-26 | 3 | Br | |
| III-27 | 2 | I | |
| III-28 | 3 | I | |

Use Examples

Example A

Pre-Emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compounds such that the particular amount of active compound desired is applied per unit area. The concentration of active compound in the spray liquor is chosen such that the particular amount of active compound desired is applied in 1000 liters of water per hectare.

After three weeks, the degree of damage to the plants is rated in % damage in comparison to the development of the untreated control. The figures denote:

0%=no effect (like untreated control)

100%=total destruction

In this test, for example, the compounds of Preparation Example 1, 2, 3, 4, 5, 6, 7, 8, 14, 15, 17, 20, 21, 24, 25 and 26 exhibit very strong activity against weeds, and some of them are tolerated well by crop plants, such as, for example, wheat and soya.

TABLE A1

| | | Pre-emergence test greenhouse | | | | | | |
|---|---|---|---|---|---|---|---|---|
| Active compound according to preparation example No. | Application rate (g of a.i./ha) | Cyperus | Echinochloa | Arbutilon | Galium | Solanum | Stellaria | Veronica |
| (3) | 8 | 100 | 100 | 100 | 100 | 100 | 100 | 100 |

TABLE A2

| | | Pre-emergence test greenhouse | | | | | | |
|---|---|---|---|---|---|---|---|---|
| Active compound according to preparation example No. | Application rate (g of a.i./ha) | Wheat | Soya | Alopecurus | Sorghum | Chenopodium | Matricaria | Viola |
| (4) | 15 | 0 | 0 | 80 | 80 | 100 | 100 | 100 |

TABLE A3

Pre-emergence test greenhouse

| Active compound according to preparation example No. | Application rate (g of a.i./ha) | Echinochloa | Amaranthus | Datura | Galium | Matricaria | Viola |
|---|---|---|---|---|---|---|---|
| (5) | 15 | 100 | 100 | 100 | 100 | 100 | 100 |

TABLE A4

Pre-emergence test greenhouse

| Active compound according to preparation example No. | Application rate (g of a.i./ha) | Wheat | Echinochloa | Chenopodium | Galium | Stellaria | Viola |
|---|---|---|---|---|---|---|---|
| (7) | 30 | 0 | 90 | 90 | 90 | 100 | 100 |
| (8) | 30 | 0 | — | 90 | 90 | 100 | 100 |

TABLE A5

Pre-emergence test greenhouse

| Active compound according to preparation example No. | Application rate (g of a.i./ha) | Wheat | Echinochloa | Chenopodium | Datura | Stellaria | Viola |
|---|---|---|---|---|---|---|---|
| (25) | 125 | 0 | 90 | 90 | 90 | 90 | 100 |

TABLE A6

Pre-emergence test greenhouse

| Active compound according to preparation example No. | Application rate (g of a.i./ha) | Alopecurus | Echinochloa | Abutilon | Amaranthus | Galium | Sinapis |
|---|---|---|---|---|---|---|---|
| (14) | 60 | 100 | 100 | 95 | 95 | 90 | 95 |
| (15) | 60 | 95 | 95 | 95 | 100 | 95 | 95 |
| (17) | 60 | 95 | 95 | 95 | 95 | 95 | 90 |

TABLE A7

Pre-emergence test greenhouse

| Active compound according to preparation example No. | Application rate (g of a.i./ha) | Alopecurus | Setaria | Abutilon | Amaranthus | Galium | Sinapis |
|---|---|---|---|---|---|---|---|
| (20) | 60 | 90 | 100 | 90 | 95 | 95 | 95 |
| (21) | 60 | 90 | 100 | 90 | 95 | 95 | 100 |
| (6) | 60 | 80 | 95 | 90 | 90 | 90 | 90 |

TABLE A8

Pre-emergence test greenhouse

| Active compound according to preparation example No. | Application rate (g of a.i./ha) | Alopecurus | Avenafatua | Setaria | Amaranthus | Galium | Xanthium |
|---|---|---|---|---|---|---|---|
| (24) | 250 | 100 | 95 | 95 | 100 | 100 | 95 |
| (1) | 250 | 100 | 100 | 100 | 100 | 100 | 100 |
| (25) | 250 | 95 | 90 | 100 | 100 | 95 | 100 |
| (26) | 250 | 100 | 90 | 100 | 100 | 95 | 95 |
| (2) | 250 | 100 | 95 | 100 | 100 | 100 | 95 |

Example B

Post-Emergence Test

Solvent: 5 parts by weight of acetone
Emulsifier: 1 part by weight of alkylaryl polyglycol ether To product a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction In this test, for example, the compounds of Preparation Example 1, 2, 3, 4, 5, 6, 7, 8, 12, 13, 14, 15, 17, 18, 20, 21, 22, 24, 25 and 26 exhibit very strong activity against weeds, and some of them are tolerated well by crop plants, such as, for example, corn, wheat and sugar beet.

TABLE B1

Post-emergence test greenhouse

| Active compound according to preparation example No. | Application rate (g of a.i./ha) | Alopecurus | Avenafatua | Setaria | Abutilon | Amaranthus | Galium | Sinapis |
|---|---|---|---|---|---|---|---|---|
| (24) | 250 | 100 | 90 | 95 | 100 | 100 | 90 | 100 |
| (1) | 250 | 95 | 95 | 100 | 100 | 100 | 100 | 100 |
| (25) | 250 | 90 | 90 | 100 | 100 | 100 | 100 | 100 |
| (26) | 250 | 95 | 90 | 90 | 100 | 100 | 90 | 95 |
| (2) | 250 | 100 | 100 | 100 | 100 | 100 | 100 | 100 |

TABLE B2

Post-emergence test greenhouse

| Active compound according to preparation example No. | Application rate (g of a.i./ha) | Wheat | Alopecurus | Abutilon | Amaranthus | Datura | Solanum |
|---|---|---|---|---|---|---|---|
| (25) | 125 | 10 | 90 | 95 | 100 | 100 | 100 |
| (7) | 30 | 0 | 90 | 100 | 100 | 100 | 100 |

TABLE B3

Post-emergence test greenhouse

| Active compound according to preparation example No. | Application rate (g of a.i./ha) | Wheat | Lolium | Abutilon | Ipomoea | Matricaria | Solanum | Stellaria |
|---|---|---|---|---|---|---|---|---|
| (17) | 8 | 10 | 90 | 100 | 100 | 100 | 100 | 100 |

TABLE B4

Post-emergence test greenhouse

| Active compound according to preparation example No. | Application rate (g of a.i./ha) | Wheat | Abutilon | Amaranthus | Matricaria | Xanthium |
|---|---|---|---|---|---|---|
| (18) | 15 | 15 | 90 | 95 | 95 | 90 |

TABLE B5

Post-emergence test greenhouse

| Active compound according to preparation example No. | Application rate (g of a.i./ha) | Wheat | Sugar beet | Amaranthus | Ipomoea | Matricaria |
|---|---|---|---|---|---|---|
| (14) | 30 | 0 | 0 | 100 | 95 | 90 |

TABLE B6

Post-emergence test greenhouse

| Active compound according to preparation example No. | Application rate (g of a.i./ha) | Wheat | Maize | Datura | Ipomoea | Matricaria | Solanum | Stellaria |
|---|---|---|---|---|---|---|---|---|
| (8) | 8 | 0 | 10 | 90 | 100 | 95 | 100 | 95 |

TABLE B7

Post-emergence test greenhouse

| Active compound according to preparation example No. | Application rate (g of a.i./ha) | Alopecurus | Abutilon | Amaranthus | Ipomoea | Matricaria | Viola |
|---|---|---|---|---|---|---|---|
| (4) | 30 | 90 | 95 | 100 | 95 | 100 | 95 |

TABLE B8

Post-emergence test greenhouse

| Active compound according to preparation example No. | Application rate (g of a.i./ha) | Alopecurus | Lolium | Abutilon | Amaranthus | Matricaria | Viola | Xanthium |
|---|---|---|---|---|---|---|---|---|
| (3) | 30 | 95 | 95 | 100 | 100 | 100 | 100 | 100 |

TABLE B9

Post-emergence test greenhouse

| Active compound according to preparation example No. | Application rate (g of a.i./ha) | Alopecurus | Abutilon | Amaranthus | Ipomoea | Xanthium |
|---|---|---|---|---|---|---|
| (6) | 30 | 90 | 90 | 90 | 100 | 95 |

TABLE B10

Post-emergence test greenhouse

| Active compound according to preparation example No. | Application rate (g of a.i./ha) | Alopecurus | Lolium | Abutilon | Amaranthus | Ipomoea | Matricaria | Stellaria |
|---|---|---|---|---|---|---|---|---|
| (5) | 30 | 95 | 95 | 100 | 100 | 100 | 100 | 100 |
| (13) | 30 | 90 | 90 | 100 | 100 | 90 | 100 | 100 |
| (15) | 30 | 90 | 90 | 95 | 100 | 100 | 100 | 100 |

TABLE B11

Post-emergence test greenhouse

| Active compound according to preparation example No. | Application rate (g of a.i./ha) | Echinochloa | Abutilon | Amaranthus | Datura |
|---|---|---|---|---|---|
| (12) | 30 | 90 | 95 | 95 | 95 |

TABLE B12

Post-emergence test greenhouse

| Active compound according to preparation example No. | Application rate (g of a.i./ha) | Echinochloa | Ipomoea | Matricaria | Polygonum | Xanthium |
|---|---|---|---|---|---|---|
| (20) | 30 | 90 | 100 | 95 | 95 | 100 |

TABLE B13

Post-emergence test greenhouse

| Active compound according to preparation example No. | Application rate (g of a.i./ha) | Avena fatua | Lolium | Datura | Matricaria | Solanum |
|---|---|---|---|---|---|---|
| (21) | 30 | 100 | 100 | 100 | 100 | 100 |

TABLE B14

Post-emergence test greenhouse

| Active compound according to preparation example No. | Application rate (g of a.i./ha) | Alopecurus | Setaria | Amaranthus | Galium | Ipomoea | Sinapis |
|---|---|---|---|---|---|---|---|
| (22) | 60 | 90 | 95 | 100 | 95 | 100 | 95 |

Example C

Podosphaera Test (Apple)/Protective

| | |
|---|---|
| Solvent: | 49 parts by weight of acetone |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

In this test, for example, the compounds of Preparation Example 1, 24, 25 and 26 exhibit, at an application rate of 100 g/ha, an efficacy of 100% against mildew of apples (*Podosphaera leucotricha*).

TABLE C

Podosphaera test (apple)/protective

| Active compound according to preparation example No. | Application rate of active compound in g/ha | % efficacy |
|---|---|---|
| 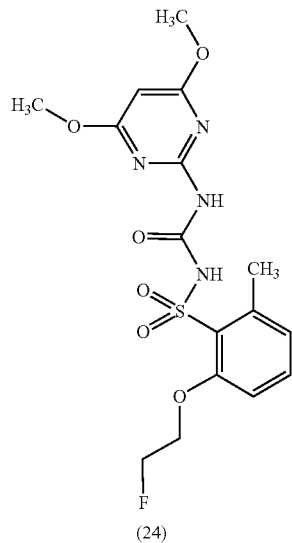 (24) | 100 | 100 |

TABLE C-continued

Podosphaera test (apple)/protective

| Active compound according to preparation example No. | Application rate of active compound in g/ha | % efficacy |
|---|---|---|
| (1) | 100 | 100 |
| (25) | 100 | 100 |

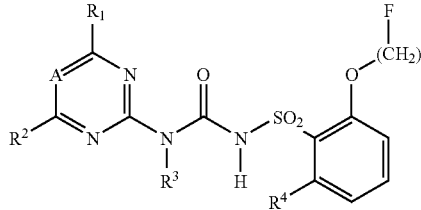

TABLE C-continued

Podosphaera test (apple)/protective

| Active compound according to preparation example No. | Application rate of active compound in g/ha | % efficacy |
|---|---|---|
| (26) | 100 | 100 |

What is claimed is:

1. A compound of formula (I)

(I)

or a salt thereof,
in which
n represents the numbers 2, 3, or 4,
A represents a group C—X,
X represents hydrogen or alkyl having in each case 1 to 4 carbon atoms,
$R^1$ represents halogen or represents alkyl or alkoxy having in each case 1 to 4 carbon atoms in the alkyl groups,
$R^2$ represents halogen or represents alkyl or alkoxy having in each case 1 to 4 carbon atoms in the alkyl groups,
$R^3$ represents hydrogen or represents alkyl having 1 to 4 carbon atoms, and
$R^4$ represents halogen, or represents optionally halogen-substituted alkyl or alkoxy having in each case 1 to 4 carbon atoms.

2. A compound according to claim 1 in which
n represents the numbers 2, 3, or 4,
A represents a group C—X,
X represents hydrogen, methyl, or ethyl,
$R^1$ represents fluorine, chlorine, or bromine, or represents methyl, ethyl, n- or -propyl, n-, i-, s-, or t-butyl, methoxy, ethoxy, n- or i-propoxy, or n-, i-, s-, or t-butoxy,
$R^2$ represents fluorine, chlorine, or bromine, or represents methyl, ethyl, n- or -propyl, n-, i-, s-, or t-butyl, methoxy, ethoxy, n- or i-propoxy, or n-, i-, s-, or t-butoxy,
$R^3$ represents hydrogen or represents methyl, ethyl, n- or t-propyl, or n-, i-, s-, or t-butyl, and R⁴ represents fluorine, chlorine, or bromine, or represents optionally fluorine-, chlorine-, or bromine-substituted methyl, ethyl, n- or -propyl, or n-, i-, s-, or t-butyl.

3. A compound according to claim 1 in which
n represents the numbers 2, 3, or 4,
A represents the group C—X,
X represents hydrogen or methyl,
R¹ represents fluorine, chlorine, or bromine, or represents methyl, ethyl, n- or i-propyl, methoxy, ethoxy, or n- or i-propoxy,
R² represents fluorine, chlorine, or bromine, or represents methyl, ethyl, n- or i-propyl, methoxy, ethoxy, or n- or i-propoxy,
R³ represents hydrogen or represents methyl, ethyl, or n- or i-propyl, and
R⁴ represents fluorine, chlorine, or bromine, or represents optionally fluorine- or chlorine-substituted methyl, ethyl, or n- or i-propyl.

4. A compound according to claim 1 in which
n represents the number 2 or 3,
A represents a CH group,
R¹ represents chlorine, methyl, ethyl, methoxy, or ethoxy,
R² represents chlorine, methyl, ethyl, methoxy, or ethoxy,
R³ represents hydrogen or methyl, and
R⁴ represents fluorine, chlorine, bromine, methyl, trifluoromethyl, ethyl, or n- or i-propyl.

5. A compound according to claim 1 in which n represents 3 or 4.

6. A process for preparing a compound according to claim 1 comprising
(a) reacting substituted an aminoazine of formula (II)

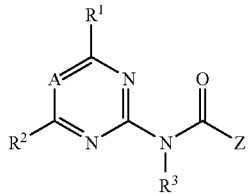

(II)

in which
A, R¹, and R² are as defined for formula (I) in claim 1,
Z represents halogen, alkoxy, or aryloxy, and
R³ is as defined for formula (I) in claim 1 or represents the group

—C(O)—Z, with a fluoroalkoxybenzenesulfonamide of formula (III)

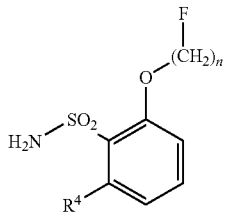

(III)

in which n and R⁴ are as defined for formula (I) in claim 1, optionally in the presence of one or more reaction auxiliaries and optionally in the presence of one or more diluents, to give a compound of formula (I), and (b) optionally, converting the resulting compound of formula (I) into a corresponding salt.

7. A method for controlling unwanted microorganisms comprising supplying one or more compounds according to claim 1 to an unwanted microorganism and/or their habitat.

8. A herbicidal or fungicidal composition comprising a compound according to claim 1 and customary extenders and/or surfactants.

* * * * *